(12) United States Patent
White et al.

(10) Patent No.: US 8,386,118 B2
(45) Date of Patent: Feb. 26, 2013

(54) SYSTEM AND METHOD FOR DETECTING AN ANOMALY IN A HIDDEN LAYER OF A MULTI-LAYER STRUCTURE

(75) Inventors: Edward V. White, St. Charles, MO (US); James P. Dunne, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 633 days.

(21) Appl. No.: 12/535,264

(22) Filed: Aug. 4, 2009

(65) Prior Publication Data
US 2011/0035088 A1    Feb. 10, 2011

(51) Int. Cl.
*G01M 17/00* (2006.01)

(52) U.S. Cl. ............... 701/29.2; 701/29.8; 701/30.8; 701/34.4; 340/438

(58) Field of Classification Search ............. 701/29.2, 701/29.7, 29.8, 30.8, 34.4; 340/438, 439
See application file for complete search history.

(56) References Cited

U.S. PATENT DOCUMENTS

| | | |
|---|---|---|
| 4,079,624 A | 3/1978 | Kurtz |
| 4,295,377 A | 10/1981 | Couchman |
| 4,342,233 A | 8/1982 | Edmondson et al. |
| 4,495,466 A | 1/1985 | Lakin |
| 4,706,387 A | 11/1987 | Wichorek |
| 4,773,272 A | 9/1988 | Trungold |
| 4,846,001 A | 7/1989 | Kibblewhite |
| 4,899,591 A | 2/1990 | Kibblewhite |
| 5,029,480 A | 7/1991 | Kibblewhite |
| 5,131,276 A | 7/1992 | Kibblewhite |
| 5,205,176 A | 4/1993 | Kibblewhite |
| 5,220,839 A | 6/1993 | Kibblewhite |
| 5,222,399 A | 6/1993 | Kropp |
| 5,379,647 A | 1/1995 | Sherwin |
| 5,437,525 A | 8/1995 | Bras |
| 5,721,380 A | 2/1998 | Gozlan |

(Continued)

FOREIGN PATENT DOCUMENTS

| | | |
|---|---|---|
| EP | 0 381 791 B1 | 4/1994 |
| WO | WO 00/50803 | 8/2000 |

(Continued)

OTHER PUBLICATIONS

U.S. Appl. No. 12/018,888, filed Jan. 24, 2008, Pado, et al.

(Continued)

*Primary Examiner* — Gertrude Arthur Jeanglaude
(74) *Attorney, Agent, or Firm* — Alston & Bird LLP

(57) ABSTRACT

Systems and methods are provided for detecting an anomaly in a hidden portion of a first layer of a multi-layer structure. A monitoring element is provided on at least one exposed end of a fastener that extends through the multi-layer structure, and another monitoring element on an exposed portion of the first layer. With at least one of the monitoring elements, an inspection signal is introduced into the multi-layer structure including the hidden portion of the first layer. The inspection signal is then sensed with at least another one of the monitoring elements following propagation of the inspection signal through at least a portion of the multi-layer structure including the hidden portion of the first layer. Finally, an anomaly may be detected in the hidden portion of the first layer based upon the inspection signal that has been sensed.

25 Claims, 2 Drawing Sheets

U.S. PATENT DOCUMENTS

| | | | |
|---|---|---|---|
| 5,798,599 | A | 8/1998 | Harwood |
| 6,006,163 | A | 12/1999 | Lichtenwalner et al. |
| 6,009,759 | A | 1/2000 | Kibblewhite et al. |
| 6,099,223 | A | 8/2000 | Galis et al. |
| 6,285,034 | B1 | 9/2001 | Hanna et al. |
| 6,715,365 | B2 | 4/2004 | Davey |
| 6,733,456 | B1 | 5/2004 | Suorsa et al. |
| 6,784,662 | B2 * | 8/2004 | Schlicker et al. ............ 324/242 |
| 6,990,866 | B2 | 1/2006 | Kibblewhite |
| 7,111,498 | B2 | 9/2006 | Jin |
| 7,117,742 | B2 | 10/2006 | Kim |
| 7,242,299 | B2 | 7/2007 | Kelsch et al. |
| 7,325,456 | B2 | 2/2008 | Kim |
| 7,528,598 | B2 | 5/2009 | Goldfine |
| 2004/0025595 | A1 | 2/2004 | Brennan |
| 2004/0065154 | A1 | 4/2004 | Kibblewhite |
| 2004/0232911 | A1 * | 11/2004 | Schlicker et al. ............ 324/242 |
| 2005/0007106 | A1 | 1/2005 | Goldfine et al. |
| 2005/0237055 | A1 | 10/2005 | Sun et al. |
| 2006/0186880 | A1 * | 8/2006 | Schlicker et al. ............ 324/242 |
| 2007/0007955 | A1 | 1/2007 | Goldfine et al. |
| 2007/0056375 | A1 | 3/2007 | Akdeniz et al. |
| 2008/0258720 | A1 | 10/2008 | Goldfine et al. |
| 2009/0099790 | A1 | 4/2009 | Pado |

FOREIGN PATENT DOCUMENTS

| | | |
|---|---|---|
| WO | WO 2004/027271 A2 | 4/2004 |

OTHER PUBLICATIONS

*Electromagnetic Smart Washer for Detecting Bolthole Cracking*, available at http://www.nasatech.com/Briefs/May98/MFS26479.html, (Mar. 31, 2005), 2 pages.

*SBIR 95-1 Solicitation, Project Summary*, available at http://www.spacepda.net/abstracts/95/sbir_html1/951449.html, (Mar. 31, 2005), 2 pages.

Goldfine, N. et al., "Material Condition and Usage Monitoring Sensors and Algorithms for Adaptive Management of Legacy and New Platforms", *Jentek Sensors*, 11 pages.

Barton, "Comparative Vacuum Monitoring: a New Method of In-situ Real-Time Crack Detection and Monitoring", 9 pages.

*The permanently mounted durable thin-film transducer*, PFW Technologies, available at http://www.pfw-tec.com/images/duennschicht_e_gr.gif, (Mar. 31, 2005), 1 page.

*Sputtering applies a permanent piezoelectric thin-layer to the bolt*, PFW Technologies, available at http://www.pfw-tec.com/en/sys2.htm, (Mar. 31, 2005), 1 page.

*Method of measuring load*, PFW Technologies, available at http://www.pfw-tec.com/images/vorspann_e_gr.gif, (Mar. 31, 2005), 1 page.

*Permanent Mounted Transducer System the system for safe bolted joints*, PFW Technologies, available at http://www.pfw-tec.com/en/sysl a.htm, (Mar. 31, 2005), 1 page.

*We are closing the confidence gap*, PFW Technologies, available at http://www.pfw-tec.com/en/untern.htm, (Mar. 31, 2005), 1 page.

*PMT System is suitable for both small series and automated bolt assembly*, PFW Technologies, available at http://pfw-tec.com/en/sys3a.htm, (Mar. 31, 2005), 1 page.

Giurgiutiu, V. et al., "New Results in the Application of E/M Impedance Method to Machinery Health Monitoring and Failure Prevention", $53^{rd}$ *Meeting of the Society for Machinery Failure Prevention Technology*, Apr. 20-22, 1999, 9 pages.

*Piezoelectric Transducers*, available at http://www.ndt-ed.org/EducationResources/CommunityCollege/Ultrasonics/EquipmentTrans/piez..., (Mar. 31, 2005), 2 pages.

Amar Kumar, et al., Sensor System for Crack Initiation and Crack Growth Monitoring in Aeroengine Components, *IEEE*, © 2007, pp. 1452-1455.

Xiaoliang Zhao, et al., Active Health Monitoring of an Aircraft Wing With Embedded Piezoelectric Sensor/Actuator Newtowrk: I. Defect Detection, Localization and Growth Monitoring, *Smart Mater, Struct.*, 16, © 2007, pp. 1208-1217.

International Search Report and Written Opinion for International Application No. PCT/US2010/040966 dated Oct. 4, 2010.

* cited by examiner

SYSTEM AND METHOD FOR DETECTING AN ANOMALY IN A HIDDEN LAYER OF A MULTI-LAYER STRUCTURE

FIELD

Embodiments of the present invention relate generally to structural health monitoring and, more particularly, to the detection of an anomaly in a hidden layer of a multi-layer structure.

BACKGROUND

A number of structures are formed of a plurality of layers that are stacked or otherwise laid one upon another to form a multi-layer structure. For example, air vehicles, such as aircraft, commonly include multi-layer structures to form various portions of the airframe. The multiple layers of a structure may be held together by one or more fasteners. In order to install a fastener, a hole may be drilled or otherwise formed through the multiple layers with a fastener thereafter being inserted through the hole. However, various anomalies may occur at or near the holes through which the fasteners extend, such as fatigue cracking due to the stress concentrations that may be present proximate the holes.

As a result of the multi-layer structure, at least portions of one or more of the layers that are proximate the hole through which the fastener extends may be hidden from view. For example, an intermediate layer of a multi-layer structure may be sandwiched between two outer layers which serve to hide the inner layer from view. By way of example, an air vehicle may include brackets mounted on longerons. The longerons may be mounted on bulkhead flanges which may, in turn, be covered by a skin. Each of these layers may be held together by one or more fasteners extending through holes that have been formed in the layers, e.g., the brackets, the longerons, the bulkhead flanges and the skin. As a result of the stacking of the various layers, portions of at least the longerons and the bulkhead flanges may be hidden from view.

Maintenance and repair personnel may desire to inspect a structure, such as an air vehicle, to identify anomalies such that the anomalies may be evaluated for repair, replacement or the like. However, the hidden layers of a multi-layer structure may not be visibly inspected and, instead, the multi-layer structure may need to be disassembled in order to view the hidden layers, such as to identify any anomalies that occurred at or near a hole through which a fastener extends. Such disassembly may be relatively labor intensive and may increase the cost and the time requirements for the inspection. Additionally, the reassembly of the structure following the inspection may also be problematic in that damage to the structure may be incurred during the reassembly process or portions of the structure may be reassembled incorrectly.

In an effort to facilitate the inspection of various structures, a variety of non-destructive evaluation ("NDE") techniques have been developed in which signals are transmitted into a structure with the signals that emerge from the structure then being evaluated in order to detect anomalies within the structure. However, NDE techniques may have difficulty in detecting anomalies in the hidden layers of a multi-layer structure due to the deleterious affect upon the signals that is created by the multiple interfaces between layers of the multi-layer structure. In addition, the thickness of a multi-layer structure may also adversely impact the ability to detect anomalies with NDE techniques where the anomalies lie within the hidden layers of the multi-layer structure.

As such, it may be desirable to provide an improved technique for inspecting the hidden layers of a multi-layer structure.

BRIEF SUMMARY

Systems and methods are provided according to embodiments of the present invention for detecting an anomaly in a hidden layer of a multi-layer structure. In this regard, systems and methods of embodiments of the present invention permit the hidden layers of a multi-layer structure to be reliably inspected without disassembly of the structure, thereby avoiding the time and cost penalties associated with disassembly and the risks introduced by reassembly.

In accordance with one embodiment, a method for detecting an anomaly in a hidden portion of a first layer of a multi-layer structure is provided. The method of this embodiment provides a monitoring element on at least one exposed end of a fastener that extends through the multi-layer structure, and another monitoring element on an exposed portion of the first layer. For example, the exposed portion of the first layer may be spaced from the hidden portion of the first layer with the hidden portion being physically inaccessible without disassembly of the multi-layer structure. With at least one of the monitoring elements, the method may then introduce an inspection signal, such as a vibration inspection signal, into the multi-layer structure including the hidden portion of the first layer. The method of this embodiment may then sense the inspection signal with at least another one of the monitoring elements following propagation of the inspection signal through at least a portion of the multi-layer structure including the hidden portion of the first layer. For example, the inspection signal may be sensed following propagation of the inspection signal through at least a portion of the fastener as well as the hidden portion of the first layer proximate the fastener. Finally, the method of this embodiment may detect an anomaly in the hidden portion of the first layer based upon the inspection signal that has been sensed.

A plurality of monitoring elements may be provided on the respective exposed portions of a plurality of layers of the multi-layer structure. In this embodiment, the plurality of layers also include respective hidden portions that may be inspected by the inspection signals that propagate through the fastener and through the respective hidden portions of the plurality of layers.

In another embodiment, a system for detecting an anomaly in a hidden portion of a first layer of a multi-layer structure is provided. The system includes a monitoring element on at least one exposed end of a fastener that extends through the multi-layer structure and another monitoring element disposed on an exposed portion of the first layer. In one embodiment, the exposed portion of the first layer is spaced from the hidden portion of the first layer with the hidden portion being physically inaccessible without disassembly of the multi-layer structure. At least one of the monitoring elements is configured to operate as an actuator for introducing an inspection signal, such as a vibration inspection signal, into the multi-layer structure including the hidden portion of the first layer. At least another one of the monitoring elements is configured to operate as a sensor for sensing the inspection signal following propagation of the inspection signal through at least a portion of multi-layer structure including the hidden portion of the first layer and, in one embodiment, following propagation of the inspection signal through at least of portion of the fastener. The system of this embodiment also includes a processor responsive to the sensor and configured to detect the anomaly in the hidden portion of the first layer based upon the inspection signal that has been sensed.

The system of one embodiment may include a plurality of monitoring elements configured to operate as sensors and disposed on respective exposed portions of a plurality of layers of a multi-layer structure. In this embodiment, the plurality of layers also includes the respective hidden portions.

In another embodiment, an aircraft is provided that includes an air frame comprising a structural component having a multi-layer structure and a fastener extending at least partially through the multi-layer structure. The multi-layer structure includes a first layer having a hidden portion proximate the fastener. The aircraft of this embodiment also includes a structural health monitoring system that may include a monitoring element on at least one exposed end of a fastener that extends through the multi-layer structure and another monitoring element disposed on an exposed portion of the first layer. In one embodiment, the exposed portion of the first layer is spaced from the hidden portion of the first layer with the hidden portion being physically inaccessible without disassembly of the multi-layer structure. At least one of the monitoring elements is configured to operate as an actuator for introducing an inspection signal, such as a vibration inspection signal, into the multi-layer structure including the hidden portion of the first layer. At least another one of the monitoring elements is configured to operate as a sensor for sensing the inspection signal following propagation of the inspection signal through at least a portion of multi-layer structure including the hidden portion of the first layer and, in one embodiment, following propagation of the inspection signal through at least of portion of the fastener. The structural health monitoring system of this embodiment also includes a processor responsive to the sensor and configured to detect the anomaly in the hidden portion of the first layer based upon the inspection signal that has been sensed.

The features, functions and advantages that have been discussed can be achieved independently in various embodiments of the present invention or may be combined in yet other embodiments, further details of which can be seen with reference to the following description and drawings.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Figure 1:
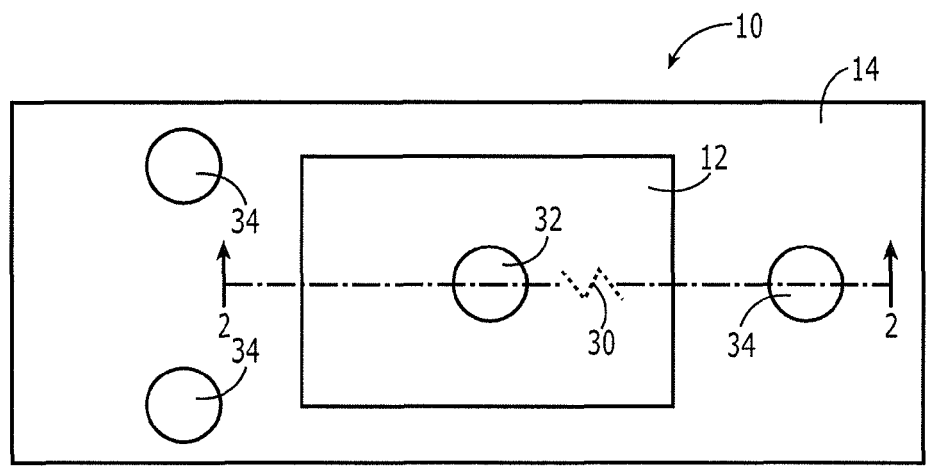
FIG. 1 is a plan view of a system in accordance with one embodiment of the present invention.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

A system and method are provided according to embodiments of the present invention for inspecting a multi-layer structure and detecting an anomaly in a hidden layer of the multi-layer structure. Various types of multi-layer structures may be inspected in accordance with embodiments of the present invention. For example, an air vehicle, such as an aircraft, may include an airframe having a structural component that includes a multi-layer structure. As shown, for example, in FIGS. 1 and 2, a multi-layer 10 structure of an airframe may include a splice plate 12 that overlies a bulkhead 14, e.g., a bulkhead flange, which, in turn, overlies a longeron 16 and the skin 18. Each of the splice plate, bulkhead, longeron and skin may be considered a layer of a multi-layer structure. Although useful for detecting anomalies in an airframe, the system and method of embodiments of the present invention may detect anomalies in other multi-layer structures that are employed in a wide variety of other applications, such as other types of vehicles, buildings, construction projects, or the like.

Regardless of the application, the layers of the multi-layer structure 10 are fastened together by means of a fastener 20, such as a bolt, a rivet or the like. In this regard, a hole 22 can be drilled, formed or otherwise defined through the plurality of layers of the multi-layer structure. The fastener may then be inserted through the hole to secure the layers together. In some embodiments in which the fastener is a threaded fastener, a nut 24 may be secured to a distal end 26 of the fastener in order to secure the fastener relative to the multi-layer structure. Thus, the fastener may extend from a first end, such as the head 28 of the fastener, through the hole defined by the multi-layer structure to a second end, such as the distal end of the fastener, upon which a nut is mounted.

Figure 2:
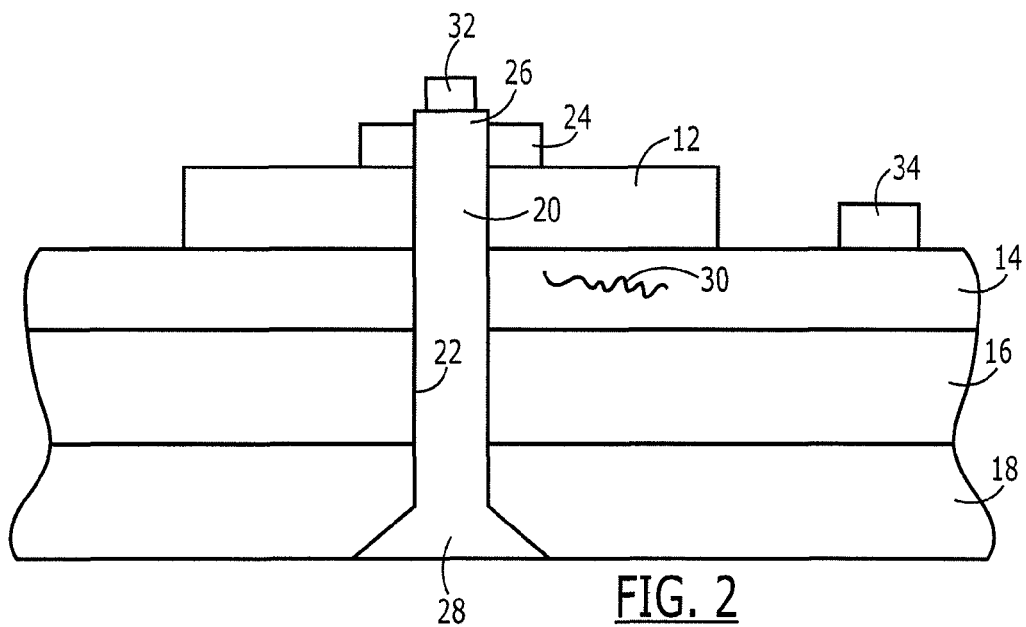
FIG. 2 is a cross-sectional view of the system of FIG. 1 taken along line 2-2.

As also depicted in FIGS. 1 and 2 and as described above, portions of one or more layers of the multi-layer structure 10 may be hidden from view as a result of other layers of the multi-layer structure overlying or otherwise being positioned upon and therefore obscuring the view of those hidden portions. The hidden portions of one or more layers of a multi-layer structure include portions that are proximate to or otherwise near the hole 22 through the multi-layer structure through which the fastener 20 extends. With reference to the illustrated embodiment of FIGS. 1 and 2, portions of the bulkhead 14 and the longeron 16 proximate the fastener are hidden from view by the splice plate 12 and the skin 18. While portions of one or more layers of the multi-layer structure may be hidden from view, other portions of those same layers, such as the bulkhead and the longeron in the embodiment of FIGS. 1 and 2, may be exposed or otherwise visible or accessible. Thus, the same layer may have both a hidden portion and an exposed portion. However, the exposed portions of one or more layers of the multi-layer structure are generally spaced apart from the fastener and may be spaced apart from the hidden portions of those same layers.

As such, one or more layers of the multi-layer structure 10, such as one or more intermediate layers, may include a hidden portion proximate the hole 22 through which the fastener 20 extends and an exposed portion spaced apart from the hole through which the fastener extends with the hidden portion being covered or otherwise visibly obstructed by another layer of the multi-layer structure, and the exposed portion being visible without being covered or otherwise obscured by any other layer of the multi-layer structure (while the multi-layer structure remains in an assembled state). By way of reference with respect to the embodiment depicted in FIGS. 1 and 2, the splice plate 12 covers the portion of the bulkhead 14 proximate the hole through which the fastener extends, with the portion of the bulkhead that is covered by the splice plate being considered a hidden portion since that portion of the bulkhead is not visible without disassembly of the multi-layer structure 10. However, other portions of the bulkhead extend beyond the splice plate and are visible, thereby constituting exposed portions of the bulkhead.

Anomalies that occur within the hidden portions of the multi-layer structure 10 are not visible, absent disassembly of the multi-layer structure 10. Various types of anomalies may be present within the hidden portions, with the anomalies occurring for various reasons, including, for example, fatigue cracking due to stress concentrations that may be present proximate the hole 22 through which the fastener 20 extends. By way of example with respect to the embodiments depicted in FIGS. 1 and 2, an anomaly 30 is illustrated in the hidden portion of the bulkhead 14 that is covered by the splice plate 12 and which is therefore out of view.

In order to facilitate the detection of anomalies within the hidden portions of a multi-layer structure 10, the system and method of embodiments of the present invention includes a structural health monitoring system that provides for monitoring elements to be disposed upon the fastener 20 and upon an exposed portion of a layer under inspection that is, the exposed portion of a layer that also has a hidden portion. See FIG. 3 and operations 50 and 52 of FIG. 4. In this regard, a monitoring element 32 may be mounted, such as by glue or another adhesive, upon one end of the fastener that extends through the hole 22 defined by the multi-layer structure. For example, the monitoring element may be mounted upon the head 24 of the fastener or the distal end 26 of the fastener, as shown in FIGS. 1 and 2. As noted above, another monitoring element 34 may be mounted, such as by glue or another adhesive, upon the exposed portion of a layer of the multi-layer structure. In this regard, the monitoring element may be mounted upon the exposed portion of a layer that also includes a hidden portion proximate the hole through which the fastener extends. With respect to the embodiment depicted in FIGS. 1 and 2, for example, a monitoring element may be mounted upon the exposed portion of the bulkhead 14 that extends beyond the splice plate 12.

In order to permit the inspection of multiple layers of a multi-layer structure 10, a plurality of monitoring elements 34 may be mounted upon the exposed portions of different layers, e.g., different intermediate layers, of the multi-layer structure. For example, one monitoring element may be mounted upon the exposed portion of the bulkhead 14, while another monitoring element may be mounted upon the exposed portion of the longeron 16. As noted above, the monitoring elements are generally mounted upon the exposed portions of layers that also include respective hidden portions proximate the hole 22 through which the fastener 20 extends. Additionally, the monitoring elements may be mounted upon either of the opposed major surfaces of the exposed portion of a layer, as opposed to the edge of the layer in order to facilitate the secure mounting of the monitoring element of the layer. While the monitoring elements may be mounted to the exposed portions of respective layers so as to be on the same side of the multi-layer structure by being mounted upon surfaces that face the same direction, the monitoring elements may be mounted to different sides or surfaces of the multi-layer structure, if so desired. Moreover, multiple monitoring elements may be mounted in different locations upon the exposed portion of the same layer in one embodiment, as shown in FIG. 1.

According to embodiments of the present invention, the monitoring elements are configured to operate either as an actuator or as a sensor. Typically, the monitoring element 32 mounted upon the fastener 20 is configured to operate as one of an actuator or a sensor, and the other monitoring element(s) 34 mounted upon the exposed portion(s) is configured to operate as the other of an actuator or a sensor. In one embodiment, for example, the monitoring element mounted upon the fastener may be configured to operate as an actuator so as to emit inspection signals, while the monitoring element(s) mounted upon the exposed portion(s) is configured to operate as a sensor for receiving the inspection signals following propagation through at least a portion of the multi-layer structure 10. Conversely, the monitoring element(s) mounted upon the exposed portion(s) may be configured to operate as an actuator in order to emit inspection signals into the multi-layer structure, while the monitoring element mounted upon the fastener may be configured to operate as a sensor for receiving the inspection signals following propagation through at least a portion of the multi-layer structure. Still further, the monitoring elements may be configured to alternately operate as an actuator and a sensor, if so desired.

The monitoring element may be configured to emit and receive various types of inspection signals. In one embodiment, however, the monitoring elements are piezoelectric transducers which are configured to operate as an actuator by converting electrical signals that are used to control or trigger the actuator into mechanical vibratory signals that are introduced as vibration inspection signals into the multi-layer structure 10, and are configured to operate as a sensor by receiving mechanical vibratory signals from the multi-layer structure and converting the mechanical vibrations into electrical signals that are thereafter analyzed as described hereinafter. However, other types of monitoring elements may be utilized, including monitoring elements that introduce and receive eddy current inspection signals, acoustic inspection signals or the like.

In the embodiment in which the monitoring element 32 mounted upon the fastener 20 is configured to operate as an actuator, the monitoring element mounted upon the fastener may be driven, triggered or otherwise actuated in order to generate inspection signals. See operation 54 of FIG. 4. These inspection signals would generally propagate along the length of the fastener. At each material interface between adjacent layers of the multi-layer structure 10, a portion of the inspection signals will propagate away from the fastener and through a respective layer of the multi-layer structure. In this regard, although not shown in FIG. 1, the multi-layer structure may also include a sealant or other type of transmission enhancement material between the fastener layers of the multi-layer structure, thereby enhancing the propagation of the inspection signals from the fastener to the hidden portions of the various layers. For those layers that include a monitoring element 34 mounted upon an exposed portion thereof, the inspection signals that are propagating through the inspection layer will be received. See operation 56 of FIG. 4. With reference to the embodiment depicted in FIGS. 1 and 2, for example, a monitoring element mounted upon the distal end 26 of the fastener proximate the splice plate 12 is configured to operate as an actuator and will be driven to emit inspection signals that will travel lengthwise along the fastener toward its head 28. A first portion of the inspection signals will propagate away from the fastener through the splice plate 12, a second portion of the inspection signals will propagate away from the fastener through the bulkhead 14, a third portion of the inspection signals will propagate away from the fastener through the longeron 16, and a fourth portion of the inspection signals will propagate away from the fastener through the skin 18. By mounting respective monitoring elements 34 upon the exposed portions of the bulkhead and the longeron, and by configuring these monitoring elements to operate as sensors, these monitoring elements may receive the inspection signals that are propagated from the fastener and through the respective layers of the multi-layer structure, that is, through the bulkhead and the longeron.

By utilizing the fastener 20 as a conduit through which the inspection signals propagate, the inspection signals may be directed into each of the layers of a multi-layer structure 10 in a manner that reduces the percentage of the inspection signals that are lost or otherwise wasted by interference, reflection, refraction or the like, such as from material interfaces between the various layers, and therefore increases that percentage of the inspection signals that are delivered to the respective layers and are thereafter generally available for detection. Additionally, by facilitating the propagation of the inspection signals between the fastener and exposed portions of the various layers, the inspection signals will propagate through the hidden portions of the layers of the multi-layer structure. With respect to the embodiment depicted in FIGS. 1 and 2, for example, the inspection signals will propagate outward from the fastener through the hidden portions of the bulkhead 14 and the longeron 16 to the monitoring elements 34 that are mounted upon the exposed portions of the bulkhead and the longeron, respectively.

The inspection signals are affected by, such as being modified by, the material through which the inspection signals propagate. In this regard, one or more anomalies in a layer, such as in the hidden portion of a layer, will cause the inspection signals to be altered, such as by causing a change in amplitude, phase, frequency or other wave propagation characteristics of the inspection signals. As a result of the propagation of the inspection signals through the hidden portions of the layers, the inspection signals that are detected by the monitoring elements 34 that are configured to operate as sensors will have been altered or otherwise affected by any anomalies within the respective hidden portions and will therefore include information indicative of any anomalies that the inspection signals have encountered.

Figure 3:
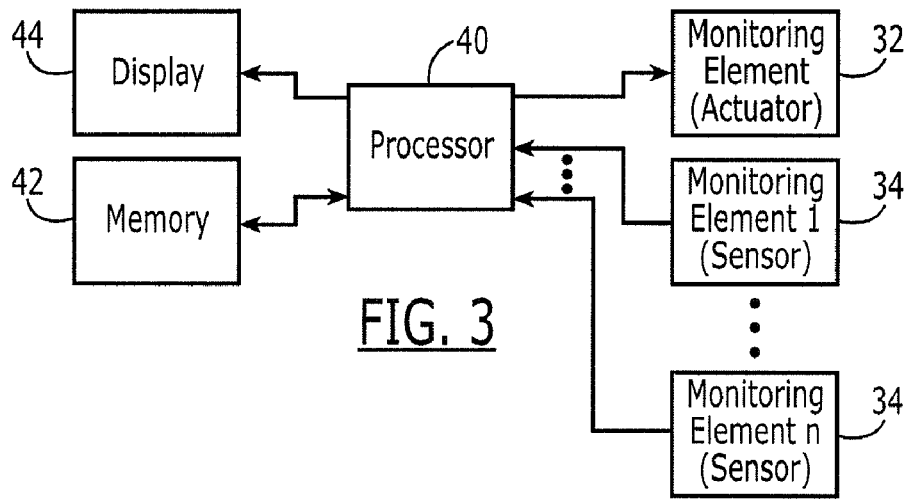
FIG. 3 is a block diagram of a system in accordance with one embodiment to the present invention.
Figure 4:
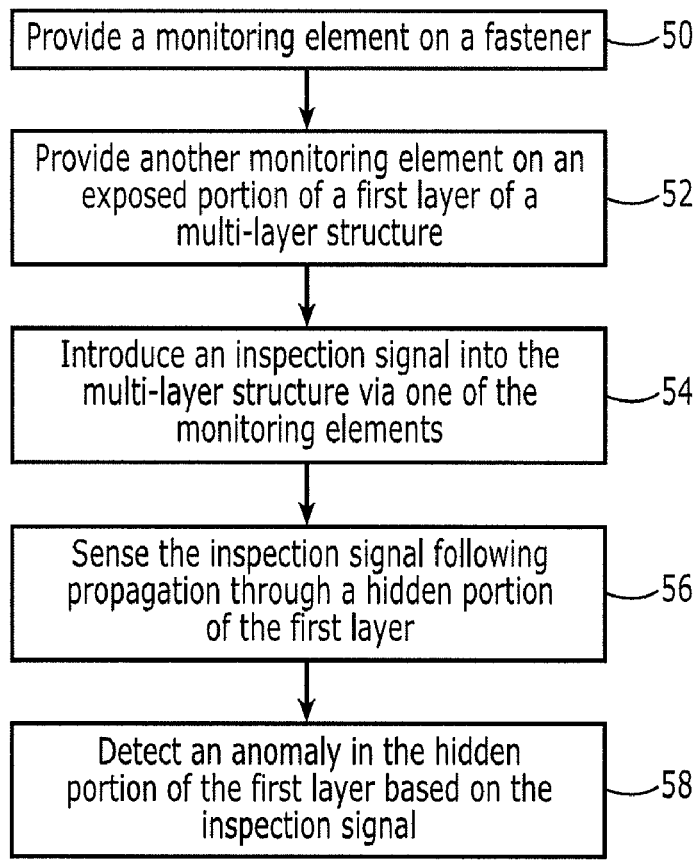
FIG. 4 is a flow chart illustrating operations performed in accordance one embodiment of the present invention.

As shown in FIG. 3, the structural health monitoring system also includes a processor 40, such as a microprocessor or other computing device, that may be in communication with and responsive to the monitoring elements 32, 34. Although the processor may be configured in various manners, the processor of one embodiment operates under the direction and control of computer program instructions, such as may be stored in a memory device 42. As such, the processor may provide triggering signals for causing the monitoring element configured to operate as an actuator to emit inspection signals, such as inspection signals having a predefined amplitude and at a predefined time. Additionally, the processor may receive the inspection signals that have been detected by the monitoring element(s) that are configured to operate as a sensor. The processor may then evaluate the inspection signals to identify inspection signals that are indicative of an anomaly within the hidden portion of a respective layer. See operation 58 of FIG. 4. If desired, the processor may store the inspection signals that have been detected and/or the results of its evaluation to identify an anomaly.

The processor 40 may be configured to identify an anomaly in various manners. For example, the processor may be configured with predefined thresholds, such as predefined amplitudes phase shift and/or time delays, and may be further configured to identify the inspection signals detected by a respective monitoring element 34 to be indicative of a respective hidden portion having an anomaly in instances in which the inspection signals do not satisfy the predefined thresholds, such as by having a lower amplitude a greater phase shift, a greater time delay or the like. Alternatively, the inspection signals that are anticipated to be received in instances in which a hidden layer has an anomaly may be defined in advance, such as by testing a sample having a known anomaly. The processor may then be configured to compare the inspection signals that are received from a respective monitoring element to the inspection signals that would be anticipated to be received following the inspection of a structure that has an anomaly. Conversely, the inspection signals that would be expected to be received in instances in which a structure is free of any anomaly may be identified in advance by testing a sample having no known anomalies. In this embodiment, the processor may be configured to compare the inspection signals that are received from a monitoring element to the predefined inspection signals in order to determine if the inspection signals that are received are the same or sufficiently close, e.g., within the predefined range, of the inspection signals that are indicative of the inspection of a structure having no anomaly or, alternatively, if the inspection signals differ from the predefined inspection signals in such a manner, such as by deviating by more than a predefined amount, so as to be indicative of a hidden portion having an anomaly. In one embodiment, the structural health monitoring system may also include a display 44 with the processor being configured to provide information, a depiction or the like regarding the anomaly upon the display.

As noted above, by utilizing the fastener 20 to facilitate the propagation of the inspection signals within or through the multi-layer structure 10, a meaningful percentage of the inspection signals are delivered to and propagate through the various layers of the multi-layer structure, thereby providing ample resolution and level of detail with respect to the identification and detection of any anomalies within the hidden portions of the layers, such as the intermediate layers, of a multi-layer structure without requiring disassembly of the multi-layer structure. In addition, the system and method of embodiments of the present invention may detect anomalies while the anomalies are relatively small and without awaiting growth or propagation of the anomaly to an exposed portion of a layer, thereby facilitating repair or other remediation efforts.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for detecting an anomaly in a hidden portion of a first layer of a multi-layer structure, the method comprising:

providing a monitoring element on at least one exposed end of a fastener that extends through the multi-layer structure;

providing another monitoring element on an exposed portion of the first layer, wherein the multi-layer structure comprises a pair of opposed surface layers through which opposite ends of the fastener extend and are exposed and one or more intermediate layers including the first layer positioned between the opposed surface layers, and wherein providing another monitoring element on an exposed portion of the first layer comprises providing another monitoring element on a surface of the first layer that extends beyond at least one of the surface layers;

introducing an inspection signal into the multi-layer structure including the hidden portion of the first layer with at least one of the monitoring elements;

sensing the inspection signal with at least another one of the monitoring elements following the propagation of the inspection signal through at least a portion of the multi-layer structure including the hidden portion of the first layer; and detecting the anomaly in the hidden portion of the first layer based upon the inspection signal that has been sensed.

2. A method according to claim 1 wherein sensing the inspection signal comprises sensing the inspection signal following propagation of the inspection signal through at least a portion of the fastener.

3. A method according to claim 1 wherein the exposed portion of the first layer is spaced apart from the hidden portion of the first layer with the hidden portion being physically inaccessible without disassembly of the multi-layer structure.

4. A method according to claim 1 wherein introducing the inspection signal comprises introducing a vibration inspection signal into the multi-layer structure.

5. A method according to claim 1 wherein providing another monitoring element comprises providing a plurality of monitoring elements on respective exposed portions of a plurality of layers of the multi-layer structure, and wherein the plurality of layers also include respective hidden portions.

6. A method according to claim 1 wherein detecting the anomaly comprises detecting the anomaly in the hidden portion of the first layer proximate the fastener.

7. A method according to claim 1 wherein providing another monitoring element on a surface of the first layer comprising providing another monitoring element on the surface of the first layer that faces in an opposite direction from the exposed end of the fastener upon which the monitoring element is provided.

8. A method according to claim 1 wherein providing the monitoring element on the at least one exposed end of the fastener comprises providing a sensor on the at least one end of the fastener, and wherein providing another monitoring element on the surface of the first layer comprises providing an actuator on the surface of the first layer.

9. A method according to claim 1 further comprising alternating operation of the monitoring element and the another monitoring element as an actuator and a sensor.

10. A method according to claim 1 further comprising providing a transmission enhancement material between the fastener and the multi-layer structure.

11. A system for detecting an anomaly, the system comprising:

a multi-layer structure comprising a pair of opposed surface layers and one or more intermediate layers including a first layer positioned between the opposed surface layers;

a monitoring element on at least one exposed end of a fastener that extends through the surface layer of the multi-layer structure another monitoring element on an exposed portion of the first layer, wherein the another monitoring element is disposed on a surface of the first layer that extends beyond at least one of the surface layers, wherein at least one of the monitoring elements is configured to operate as an actuator for introducing an inspection signal into the multi-layer structure including a hidden portion of the first layer, and wherein at least another one of the monitoring elements is configured to operate as a sensor for sensing the inspection signal following the propagation of the inspection signal through at least a portion of the multi-layer structure including the hidden portion of the first layer; and a processor responsive to the sensor and configured to detect an anomaly in the hidden portion of the first layer based upon the inspection signal that has been sensed.

12. A system according to claim 11 wherein the sensor is configured to sense the inspection signal following propagation through at least a portion of the fastener.

13. A system according to claim 11 wherein the exposed portion of the first layer is spaced apart from the hidden portion of the first layer with the hidden portion being physically inaccessible without disassembly of the multi-layer structure.

14. A system according to claim 11 wherein the actuator is configured to introduce a vibration inspection signal into the multi-layer structure.

15. A system according to claim 11 further comprising a plurality of monitoring elements configured to operate as sensors and disposed on respective exposed portions of a plurality of layers of the multi-layer structure, and wherein the plurality of layers also include respective hidden portions.

16. A system according to claim 11 wherein the multi-layer structure comprises a plurality of structural elements of an aircraft, and wherein the processor is configured to detect the anomaly in the hidden portion of the first layer proximate the fastener.

17. A system according to claim 11 wherein the another monitoring element is disposed on the surface of the first layer that faces in an opposite direction from the exposed end of the fastener upon which the monitoring element is provided.

18. A system according to claim 11 wherein the monitoring element on the at least one exposed end of the fastener comprises an actuator.

19. A system according to claim 11 wherein the monitoring element and the another monitoring element are configured to alternately operate as an actuator and a sensor.

20. A system according to claim 11 further comprising a transmission enhancement material between the fastener and the multi-layer structure.

21. An aircraft comprising:

an airframe comprising a structural component having a multi-layer structure and a fastener extending at least partially through the multi-layer structure, wherein the multi-layer structure comprises a pair of opposed surface layers through which opposite ends of the fastener extend and are exposed and one or more intermediate layers including a first layer positioned between the opposed surface layers with the first layer having a hidden portion proximate the fastener;

a structural health monitoring system comprising: a monitoring element on at least one exposed end of a fastener that extends through the multi-layer structure and another monitoring element on an exposed portion of the first layer, wherein the another monitoring element is disposed on a surface of the first layer that extends beyond at least one of the surface layers, wherein at least one of the monitoring elements is configured to operate as an actuator for introducing an inspection signal into the multi-layer structure including the hidden portion of the first layer, and wherein at least another one of the monitoring elements is configured to operate as a sensor for sensing the inspection signal following the propagation of the inspection signal through at least a portion of the multi-layer structure including the hidden portion of the first layer; and a processor responsive to the sensor and configured to detect the anomaly in the hidden portion of the first layer based upon the inspection signal that has been sensed.

22. An aircraft according to claim 21 wherein the sensor is configured to sense the inspection signal following propagation through at least a portion of the fastener.

23. An aircraft according to claim 21 wherein the exposed portion of the first layer is spaced apart from the hidden portion of the first layer with the hidden portion being physically inaccessible without disassembly of the multi-layer structure.

24. An aircraft according to claim 21 wherein the actuator is configured to introduce a vibration inspection signal into the multi-layer structure.

25. An aircraft according to claim 21 further comprising a plurality of monitoring elements configured to operate as sensors and disposed on respective exposed portions of a plurality of layers of the multi-layer structure, and wherein the plurality of layers also include respective hidden portions.

* * * * *